United States Patent [19]

Yankee

[11] 4,122,101
[45] Oct. 24, 1978

[54] CIS-13-PGA$_1$ ANALOGS

[75] Inventor: Ernest W. Yankee, Portage, Mich.

[73] Assignee: The Upjohn Company, Kalamazoo, Mich.

[21] Appl. No.: 774,178

[22] Filed: Mar. 3, 1977

Related U.S. Application Data

[62] Division of Ser. No. 595,869, Jul. 14, 1975, Pat. No. 4,026,909.

[51] Int. Cl.$^2$ ............................................ C07C 177/00
[52] U.S. Cl. .................................... 260/408; 260/410; 260/410.5; 260/410.9 R; 260/413; 560/121; 562/503
[58] Field of Search .............. 260/468 D, 514 D, 408, 260/410, 410.9 R, 413, 410.5; 560/121

[56] References Cited

U.S. PATENT DOCUMENTS 3,932,479   1/1976   Bernady et al. ..................... 260/448

*Primary Examiner*—Robert Gerstl
*Attorney, Agent, or Firm*—Robert A. Armitage

[57] ABSTRACT

This invention comprises certain analogs of the prostaglandins in which the double bond between C-13 and C-14 is of the cis configuration. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

49 Claims, No Drawings

CIS-13-PGA₁ ANALOGS

The present application is a divisional application of Ser. No. 595,869, filed July 14, 1975, now issued as U.S. Pat. No. 4,026,909 on May 31, 1977.

The present invention relates to prostaglandin analogs for which the essential material constituting a disclosure therefor is incorporated by reference here from U.S. Pat. No. 4,026,909, issued May 31, 1977.

I claim:

1. A compound of the formula

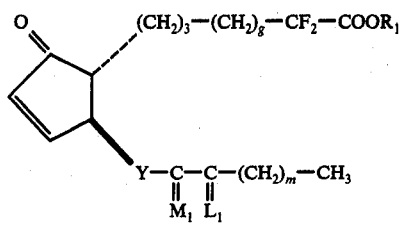

wherein Y is cis—CH=CH—;
wherein $g$ is 2, 3, or 4;
wherein $M_1$ is

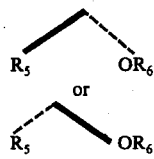

wherein $R_5$ and $R_6$ are hydrogen or methyl, with the proviso that one of $R_5$ and $R_6$ is methyl only when the other is hydrogen;
wherein $L_1$ is

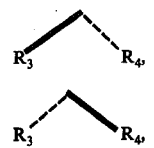

or a mixture of

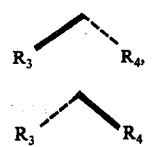

wherein $R_3$ and $R_4$ are hydrogen, methyl, fluoro, being the same or different, with the proviso that one of $R_3$ and $R_4$ is fluoro only when the other is hydrogen or fluoro;
wherein $m$ is 1 to 5, inclusive; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein $g$ is 2.
3. A compound according to claim 2, wherein $m$ is 3.
4. A compound according to claim 3, wherein at least one of $R_3$ and $R_4$ is fluoro.
5. A compound according to claim 4, wherein $R_3$ and $R_4$ are both fluoro.
6. A compound according to claim 5, wherein $R_5$ and $R_6$ are hydrogen.
7. 15-epi-2,2,16,16-Tetrafluoro-cis-13-PGA₁, methyl ester, a compound according to claim 6.
8. A compound according to claim 3, wherein at least one of $R_3$ and $R_4$ is methyl.
9. A compound according to claim 8, wherein $R_3$ and $R_4$ are both methyl.
10. A compound according to claim 9, wherein $R_5$ and $R_6$ are both hydrogen.
11. 15-epi-2,2-Difluoro-16,16-dimethyl-cis-13-PGA₁, methyl ester, a compound according to claim 10.
12. A compound according to claim 3, wherein $R_3$ and $R_4$ are both hydrogen.
13. A compound according to claim 12, wherein $R_5$ and $R_6$ are both hydrogen.
14. 15-epi-2,2-Difluoro-cis-13-PGA₁, methyl ester, a compound according to claim 13.
15. A compound according to claim 12, wherein $R_5$ is methyl.
16. 15-epi-2,2-Difluoro-15-methyl-cis-13-PGA₁, methyl ester, a compound according to claim 15.
17. A compound according to claim 12, wherein $R_6$ is methyl.
18. 15-epi-2,2-Difluoro-cis-13-PGA₁, 15-methyl ether, methyl ester, a compound according to claim 17.
19. A compound of the formula

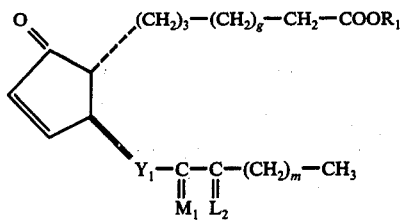

wherein $Y_1$ is cis—CH=CH—;
wherein $g$ is 2, 3, or 4;
wherein $M_1$ is

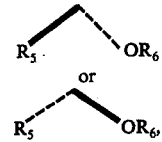

wherein $R_5$ and $R_6$ are hydrogen or methyl, with the proviso that one of $R_5$ and $R_6$ is methyl only when the other is hydrogen;
wherein $L_2$ is

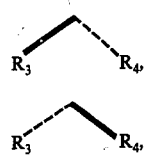

or a mixture of

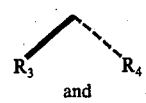

and

-continued

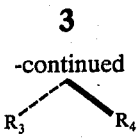

wherein $R_3$ and $R_4$ are hydrogen or fluoro, being the same or different, with the proviso that at least one of $R_3$ and $R_4$ is fluoro;
wherein m is one to 5, inclusive; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

20. A compound according to claim 19, wherein g is 4.

21. A compound according to claim 20, wherein m is 3.

22. A compound according to claim 21, wherein $R_3$ and $R_4$ are both fluoro.

23. A compound according to claim 22, wherein $R_5$ and $R_6$ are hydrogen.

24. 15-epi-2a,2b-Dihomo-16,16-difluoro-cis-13-PGA$_1$, methyl ester, a compound according to claim 23.

25. A compound according to claim 19, wherein g is 2.

26. A compound according to claim 25, wherein m is 3.

27. A compound according to claim 26, wherein both $R_3$ and $R_4$ are fluoro.

28. A compound according to claim 27, wherein $R_5$ and $R_6$ are hydrogen.

29. 15-epi-16,16-difluoro-cis-13-PGA$_1$, methyl ester, a compound according to claim 28.

30. A compound of the formula

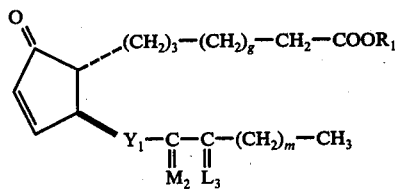

wherein Y is cis—CH=CH—;
wherein g is 2, 3, or 4;
wherein $M_2$ is

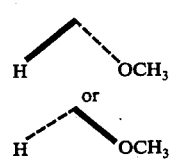

wherein $L_3$ is

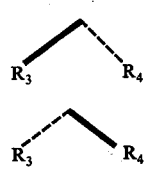

or a mixture of

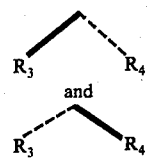

wherein $R_3$ and $R_4$ are hydrogen or methyl, being the same or different;
wherein m is one to 5, inclusive; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

31. A compound according to claim 30, wherein g is 2.

32. A compound according to claim 31, wherein m is 3.

33. A compound according to claim 32, wherein at least one of $R_3$ and $R_4$ is methyl.

34. A compound according to claim 32, wherein $R_3$ and $R_4$ are both methyl.

35. A compound according to claim 32, wherein $R_3$ and $R_4$ are hydrogen.

36. 15-epi-cis-13-PGA$_1$, methyl ester, 15-methyl ether, a compound according to claim 35.

37. A compound of the formula

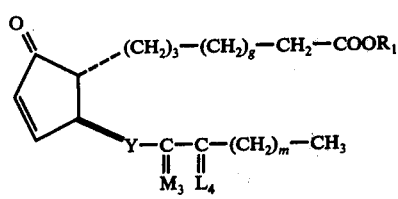

wherein Y is cis—CH=CH—;
wherein $M_3$ is

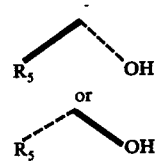

wherein $R_5$ is hydrogen or methyl;
wherein $L_4$ is

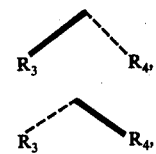

or a mixture of

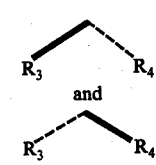

wherein $R_3$ and $R_4$ are hydrogen or methyl, being the same or different, with the proviso that one of $R_3$ and $R_4$ is methyl;

wherein $m$ is 1 to 5, inclusive; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

38. A compound according to claim 37, wherein $g$ is 4.

39. A compound according to claim 38, wherein $m$ is 3.

40. A compound according to claim 39, wherein $R_3$ and $R_4$ are both methyl.

41. A compound according to claim 40, wherein $R_5$ is hydrogen.

42. 15-epi-2a,2b-Dihomo-16,16-dimethyl-cis-13-$PGA_1$, methyl ester, a compound according to claim 41.

43. A compound according to claim 37, wherein $g$ is 2.

44. A compound according to claim 43, wherein $m$ is 3.

45. A compound according to claim 44, wherein $R_3$ and $R_4$ are both methyl.

46. A compound according to claim 45, wherein $R_5$ is hydrogen.

47. 15-epi-16,16-Dimethyl-cis-13-$PGA_1$, methyl ester, a compound according to claim 46.

48. A compound of the formula

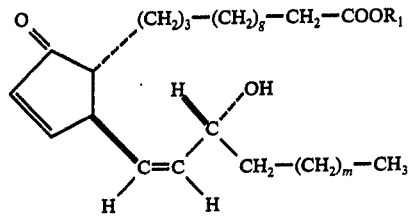

or a mixture comprising that compound and the enantiomer thereof;

wherein $g$ is 2 to 4;

wherein $m$ is 1 to 5; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two or three chloro or alkyl of one to 3 carbon atoms, inclusive, or a pharmacologically acceptable cation.

49. 15-epi-cis-13-$PGA_1$, methyl ester, a compound according to claim 48.

* * * * *

UNITED STATES PATENT OFFICE
CERTIFICATE OF CORRECTION

Patent No. 4,122,101　　　　　　　　　Dated October 24, 1978

Inventor(s)　　　Ernest W. Yankee

It is certified that error appears in the above-identified patent and that said Letters Patent are hereby corrected as shown below:

Column 3, line 49, "wherein Y is" should read -- wherein $Y_1$ is --.

Signed and Sealed this

Sixth Day of March 1979

[SEAL]

Attest:

RUTH C. MASON　　　　　　　　　DONALD W. BANNER
Attesting Officer　　　　　　　Commissioner of Patents and Trademarks